US00PP11154P

United States Patent [19]

Kordes

[11] Patent Number: Plant 11,154

[45] Date of Patent: Dec. 14, 1999

[54] MINIATURE ROSE PLANT NAMED 'KORPROLIT'

[75] Inventor: Wilhelm Kordes, Sparrieshoop, Germany

[73] Assignee: Bear Creek Gardens, Inc., Medford, Oreg.

[21] Appl. No.: 09/073,020

[22] Filed: May 4, 1998

[51] Int. Cl.[6] ..... A01H 5/00

[52] U.S. Cl. ..... Plt./121

[58] Field of Search ..... Plt./120, 121, 127, Plt./128

*Primary Examiner*—Howard J. Locker

*Attorney, Agent, or Firm*—Klarquist Sparkman Campbell Leigh & Whinston, LLP

[57] ABSTRACT

Miniature rose plant having a compact, well branched growing habit; ease of rooting from softwood cuttings; long shelf life; and stable flower color.

1 Drawing Sheet

The present invention relates to a new and distinct variety of rose plant of the miniature class which was originated by me by crossing the varieties 'KORialie', with an unnamed seedling.

The primary objective of this breeding was to produce a new miniature rose variety having a compact, well branched growing habit, ease of rooting from softwood cuttings; long shelf life; and stable flower color. The objective was substantially achieved, along with other desirable improvements, as evidenced by the following unique combination of characteristics that are outstanding in the new variety and that distinguish it from its parents, as well as from all other varieties of which I am aware:

1. Compact, well branched growth habit;
2. Base of rooting from softwood cuttings;
3. Stable flower color;
4. Long shelf life;
5. Rapid growth and ease of flowering.

Asexual reproduction of this new variety by cutting propagation, as performed at Sparrieshoop, Germany, and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—'KORialie' (unpatented).

*Pollen parent*.—Unnamed seedling.

Classification:

*Botanical*.—Rosa hybrida.

*Commercial*.—Miniature rose.

FLOWER

Observations made from specimens grown in a greenhouse environment at Sparrieshoop, Germany and at Somis, Calif. from January, 1997 to February, 1998.

Blooming habit: Continuous.

Bud:

*Size*.—Three-quarters inch long when the petals start to unfurl.

*Form*.—The bud form is long, pointed ovoid.

*Color*.—When sepals first divide, bud color is Red Group 37D. When half blown, the upper sides of the petals are Red Group 37D and the lower sides of the petals are all Red Group 37D.

*Sepals*.—Color: Green group 137D. Surface texture: Covered in fine hairs. There are three lightly appendaged sepals. There are two unappendaged sepals with hairy edges.

*Receptacle*.—Color: Green Group 137B. Shape: Funnel. Size: Small (¼"×3/16"). Surface: Smooth.

*Peduncle*.—Length: Short (1½–1¾"). Color: Green Group 137C with immature peduncles having a bronze cast of Greyed-Red Group 178B. Strength: Stiff, erect.

Bloom:

*Size*.—Small. Average open size is 1¾ inches.

*Borne*.—Singly or in pyramidal clusters of three to five blooms.

*Stems*.—Short, strong. Average length is about five and one-half to six inches.

*Form*.—When first open: High centered. Permanence: Flattens, all petals curl.

*Petalage*.—Number of petals under normal conditions 40–45.

*Color*.—The upper sides of the petals are Red Group 37D. The reverse sides of the petals are Red Group 37D. The base of each petal has a small (1 1/16"×⅛"), White Group 155D, half moon at the point of attachment. The major color on the upper sides is Red Group 37D.

*Variegations*.—Occasional greenish-white streak on the guard petals.

*Discoloration*.—At the end of the first day: No change. At the end of the third day: No change. By day twelve or thirteen there is a fading of the individual flower to near Red Group 38D. Petal drop occurs day sixteen to eighteen.

*Fragrance*.—None.

Petals:

*Texture*.—Leathery.

*Shape*.—Round to deltoid.

*Form*.—Tips slightly recurved, edges slightly quilled.

*Arrangement*.—Imbricated. Petaloids in the center are few and small.

*Persistence*.—Petals drop off cleanly before drying.

*Lastingness*.—On the plant: Very long (about sixteen days). As a cut flower: Very long (about twenty days).

Reproductive parts:

*Anthers*.—Size: Medium. Quantity: Many. Color: Yellow. Arrangement: Regular around styles.

*Filaments*.—Color: Yellow.

*Pollen*.—Color: Gold yellow.

*Styles*.—Color: Greenish-white.

*Stigmas*.—Color: Greenish-White.

Plant:

*Form*.—Bush.

*Growth*.—Vigorous; upright; branching; compact. In a garden setting, at maturity, height is twenty to twenty-two inches tall, width is sixteen to twenty inches. When grown as a pot rose in a 10 cm pot, the plant is eight to nine inches in height and seven to eight inches wide.

Foliage: Number of leaflets on normal mid-stem leaves: Five.

*Size*.—Small (2½" long ×1¾" wide).

*Quantity*.—Abundant.

*Color*.—New foliage: Upper and lower surfaces: Greyed-Red Group 178B. Old foliage: Upper surface: Green Group 139A. Lower surface: Green Group 139C.

*Shape*.—Pointed oval.

*Texture*.—Upper side: Leathery, glossy,

*Edge*.—Serrated.

*Serration*.—Single, small.

*Petiole rachis*.—Color: Greyed-Purple Group 183B.

*Petiole underside*.—Smooth with some glands.

*Stipules*.—Short (¼"), serrated.

*Disease resistance*.—Resistant to mildew under normal growing conditions in the greenhouse at Sparriehoop, Germany and Somis, Calif.

Wood:

*New wood*.—Color: Greyed-Red Group 178B. Bark: Smooth.

*Old wood*.—Color: Green Group 137C. Bark: Smooth.

Prickles:

*Quantity*.—On main canes from base: Few. On laterals from main canes: Few.

*Form*.—Short, hooked downward.

*Color when young*.—Greyed- Purple Group 183D.

Small prickles:

*Quantity*.—On main stalks: None. On laterals: None.

I claim:

1. A new and distinct variety of miniature rose plant as herein shown and described characterized particularly by a compact, well branched growing habit; ease of rooting from softwood cuttings; long shelf life; and stable flower color.

* * * * *

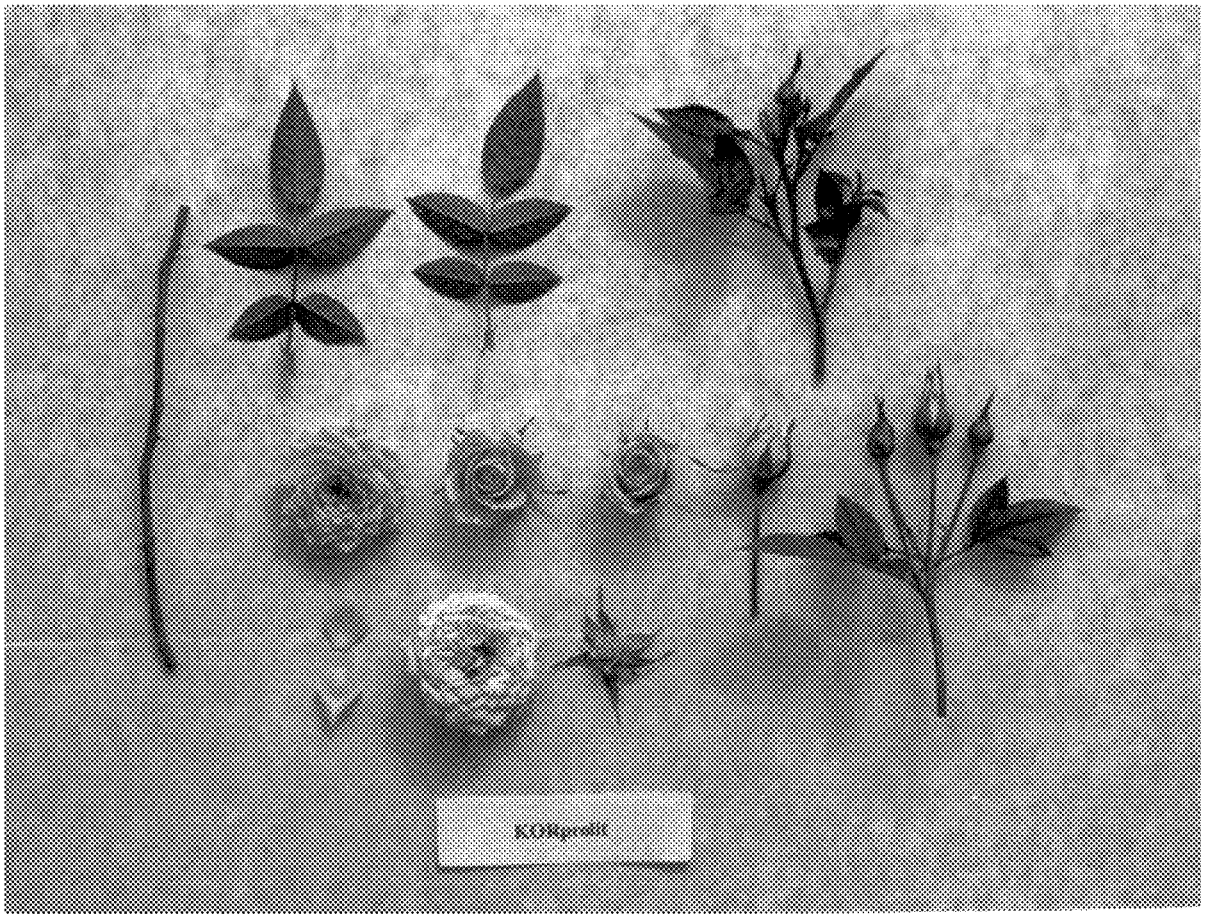

UNITED STATES PATENT AND TRADEMARK OFFICE

CERTIFICATE OF CORRECTION

PATENT NO. : PP11,154
DATED : December 14, 1999
INVENTOR(S) : Wilhelm Kordes

It is certified that error appears in the above-identified patent and that said Letters Patent is hereby corrected as shown below:

In the Specification:

Column 1,
Line 15, reads "Base". It should read --Ease--.

Column 2,
Line 16, before "Color:", insert --Surface: Smooth with a few glands.--.

Signed and Sealed this

Third Day of July, 2001

Nicholas P. Godici

*Attest:*

*Attesting Officer*

NICHOLAS P. GODICI
*Acting Director of the United States Patent and Trademark Office*